(12) United States Patent
Yarger

(10) Patent No.: US 7,125,402 B1
(45) Date of Patent: Oct. 24, 2006

(54) SURGICAL DRAIN

(75) Inventor: Richard J. Yarger, Yakima, WA (US)

(73) Assignee: Surgimark, Inc., Yakima, WA (US)

( * ) Notice: Subject to any disclaimer, the term of this patent is extended or adjusted under 35 U.S.C. 154(b) by 388 days.

(21) Appl. No.: 10/447,722

(22) Filed: May 27, 2003

Related U.S. Application Data

(60) Provisional application No. 60/384,150, filed on May 29, 2002.

(51) Int. Cl.
*A61M 1/00* (2006.01)
*A61M 27/00* (2006.01)
*A61M 25/20* (2006.01)

(52) U.S. Cl. ..................... 604/541; 604/266

(58) Field of Classification Search .............. 604/266, 604/268, 276, 540–544, 523, 43, 508, 129, 604/267, 524, 902; D24/112, 118, 130
See application file for complete search history.

(56) References Cited

U.S. PATENT DOCUMENTS

| | | | | |
|---|---|---|---|---|
| 1,596,754 A | * | 8/1926 | Moschelle | 604/541 |
| 1,928,992 A | * | 10/1933 | Masterman et al. | 138/103 |
| 4,257,422 A | * | 3/1981 | Duncan | 604/266 |
| 4,465,481 A | * | 8/1984 | Blake | 604/541 |
| 4,523,920 A | * | 6/1985 | Russo | 604/266 |
| 4,650,463 A | * | 3/1987 | LeVeen et al. | 604/43 |
| 4,717,379 A | * | 1/1988 | Ekholmer | 604/43 |
| 4,950,232 A | * | 8/1990 | Ruzicka et al. | 604/43 |
| 5,116,310 A | * | 5/1992 | Seder et al. | 604/43 |
| 5,360,414 A | * | 11/1994 | Yarger | 604/264 |
| 6,099,513 A | * | 8/2000 | Spehalski | 604/264 |
| 6,478,789 B1 | * | 11/2002 | Spehalski et al. | 604/540 |
| 6,866,657 B1 | * | 3/2005 | Shchervinsky | 604/266 |
| 6,893,424 B1 | * | 5/2005 | Shchervinsky | 604/264 |

FOREIGN PATENT DOCUMENTS

| | | | |
|---|---|---|---|
| EP | 0 457 220 A1 | * | 5/1991 |
| EP | 1 364 665 A1 | * | 11/2005 |
| FR | 2.170.858 | * | 9/1973 |
| GB | 1 531 416 | * | 11/1978 |

\* cited by examiner

*Primary Examiner*—Tatyana Zalukaeva
*Assistant Examiner*—Michael G. Bogart
(74) *Attorney, Agent, or Firm*—Christensen O'Connor Johnson Kindness PLLC

(57) ABSTRACT

An improved surgical drain tube 10 having an internal passageway 12, a plurality of portions 14 of the external wall of the tube extending outwardly and being arranged in opposing pairs, the walls of the outwardly extending portions forming the sidewalls 14A, 14B, 16 of external channels 18 that run longitudinally along the length of the tube, and crossholes 20 positioned on the sidewalls of the outwardly extending portions 14 that provide for fluid flow from the channel 18 into the internal passageway 12 of the tube.

25 Claims, 2 Drawing Sheets

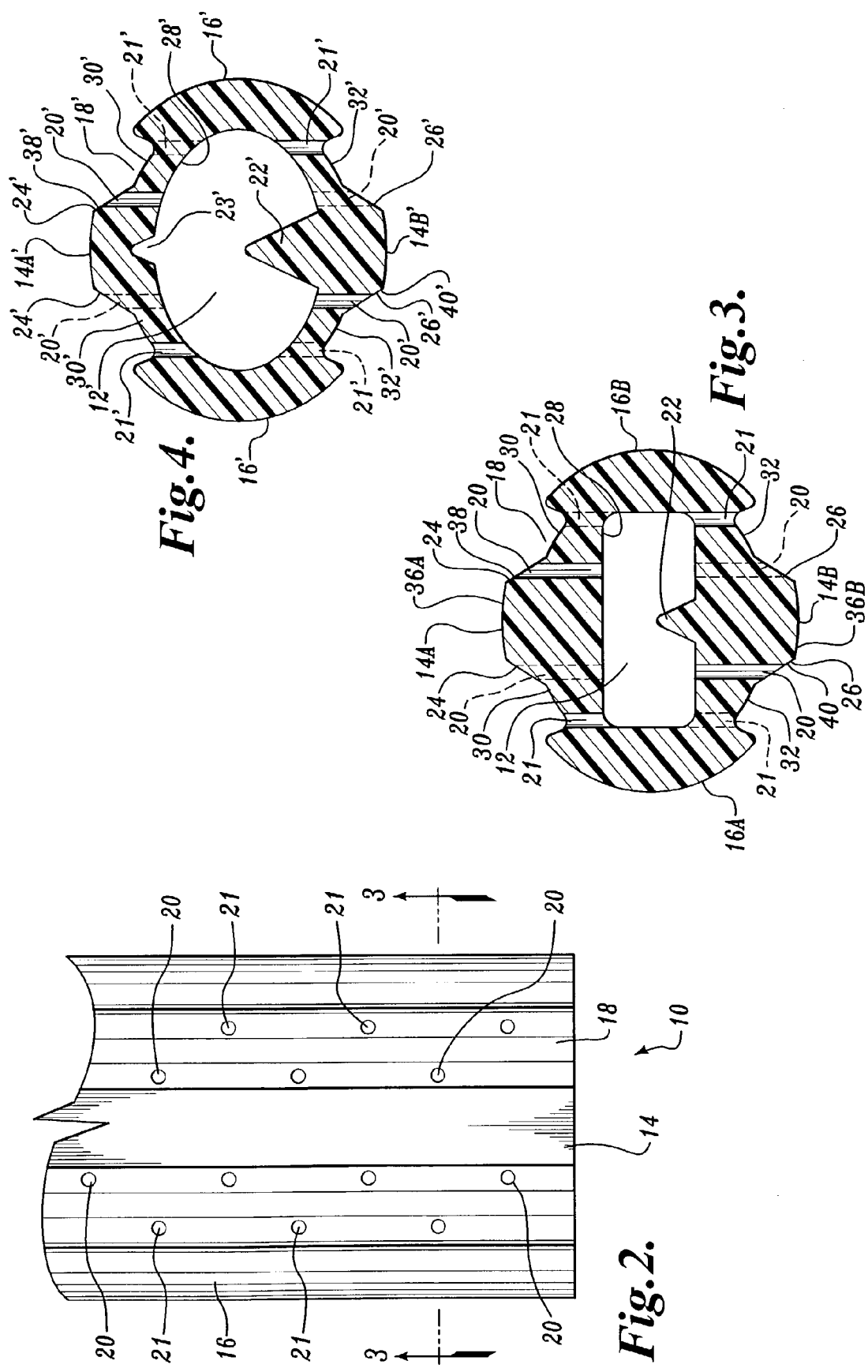

SURGICAL DRAIN

CROSS-REFERENCE TO RELATED APPLICATION

This application claims the benefit of U.S. Provisional Application No. 60/384,150, filed May 29, 2002.

FIELD OF THE INVENTION

The present invention pertains to a drainage tube for removing excess fluids from body cavities, surgical sites, wounds, and the like.

BACKGROUND OF THE INVENTION

Surgical invasion of the body generally results in trauma and to an accumulation of fluids from the traumatized tissue itself or from the circulatory system. To avoid the build-up of pressure and to minimize the danger of infection, it is desirable that such fluids be removed from the surgical site. Accidentally inflicted wounds also are subject to similar fluid build-ups, and will heal faster if the excess fluids are drained and are prevented from re-accumulating. In such cases, it is common practice to install a drain tube designed for this purpose, and to leave this tube in place to provide for continuous fluid removal until the accumulation has abated.

A variety of drainage tubes or catheters have been devised for removing excess fluids from postsurgical sites or wounds. Such drains often employ external grooves to collect the fluids, or contain perforations through which fluids can enter a central passageway that carries the fluids away from the site. In many cases, suction is applied to the external end of the tube to aid in the fluid removal. One problem with existing drainage tubes and catheters is that when a drainage device is left in place for any length of time, tissue often grows into the drain, especially into its perforations, thus hindering and rendering very painful the drain's eventual removal from the body. Thus, an optimal drain design is one that efficiently removes unwanted fluids, but that minimizes the tendency of tissues to grow into the drain. Previous drain designs have approached these goals in different ways.

U.S. Pat. No. 5,360,414 provides a drain having a circular internal passageway and several externally extending portions whose walls curve inwardly to form a number of relatively small external lumens that run lengthwise along the external surface of the drain. The curved walls forming the lumens do not quite meet, thus providing a groove-like opening into which fluid can enter. The drain itself is interrupted by several perforations that are large enough to intersect more than one of the external lumens, and that provide a means for fluid enter the central passageway.

U.S. Pat. No. 4,650,463 describes a tube for surgical drainage that has an internal passageway formed in a cloverleaf cross-section, and that has an external channel formed by outwardly extending portions of the tubing wall that curve towards each other to form the channel. Perforations located at the bottom of the external lumen connect the lumen with the internal passageway to provide for fluid flow into the internal passageway of the tube.

U.S. Pat. No. 4,573,965 discloses a drain tube with smooth exterior walls and having two lumens, and which is perforated at one end. This drain features an antibacterial filter and a check valve that are mounted in-line within the second lumen.

U.S. Pat. No. 4,543,089 provides a drain consisting of a thick walled tube having two closed lumens situated entirely within the wall, one of which is used for feeding fluids into the body or wound, the other of which is used for aspiration.

U.S. Pat. No. 4,531,935 describes an aspiration cannula assembly for use during heart surgery in delivering cardioplegic fluid to and aspirating air from the aorta. The device provides an inner cannula for delivering fluids, which is enclosed within an outer cannula that has a plurality of holes through which air can be aspirated.

U.S. Pat. No. 4,465,481 describes a wound drain catheter having a drain segment, a transition tube segment, and an extrusion tube segment. The drain segment lacks a central passageway, but provides several external longitudinal channels that are formed by outwardly projecting extruding portions of the tube.

U.S. Pat. No. 4,445,897 discloses a surgical drain catheter that has a central passageway and one or more external slots or lumens that extend longitudinally along the catheter. Perforations located at the bottom of the external lumens connect them to the central passageway of the main tube to provide for fluid flow.

U.S. Pat. No. 3,771,527 discloses a surgical drain comprising inner and outer tubes, one within the other, which are arranged so that fluid can be introduced through one tube into the body cavity while suction is simultaneously applied to remove excess fluids from the site through the other tube. The inner wall of the outer tube is equipped with inwardly extending ribs to prevent its collapse against the inner tube. Both the inner and outer tubes are perforated to allow for the flow of fluids.

U.S. Pat. No. 3,599,641 discloses a catheter having multiple internal lumens that provide a principal channel and one or more secondary channels, with an opening through the sidewall of the catheter at the proximal end to provide access to the secondary channel.

U.S. Pat. No. 3,020,913 discloses a surgical drain comprising a flexible tube with an inner and outer wall. An inlet means is provided by holes between the two walls, which connect the passage to the outside of the tube at one location to let fluid drain into the passage. The outlet means comprises an axial slit that extends through the tube between the walls, and is designed so that the slit is closed when the tube is compressed on both walls. Thus, the slit will open to let fluid escape from the passage when the pressure inside the passage exceeds the external pressure on the outside walls of the tube.

U.S. Pat. No. 1,596,754 describes a surgical drain designed to resist collapsing by virtue of two pair of internally located ribs that run longitudinally inside the internal passageway of the smooth-surfaced drain tube.

U.S. Pat. No. 2,930,378 describes an abdominal drain tube, closed at one end, consisting of flexible inner and outer tubes, one running within the other, both tubes being perforated.

U.S. Pat. No. 1,045,326 discloses a flexible irrigating catheter closed at one end and designed for introducing fluids into body cavities, and for causing a return flow of the irrigating liquid on the exterior of the catheter. This catheter has an internal passageway and also has external open U-shaped channels arranged longitudinally along its exterior surface, the channels being designed to provide for the return flow of the irrigating fluid. Perforations situated at the bottoms of the open channels connect the channels with the internal passageway.

Despite the above-described approaches to providing drains or catheters for removing excess fluid from the body, there has remained a need for new and improved methods for such drainage, particularly methods that minimize or eliminate the problem of occlusion of the drain by debris in a wound or the ingrowth of living tissue surrounding the wound during the time it is left in place.

SUMMARY OF THE INVENTION

The present invention provides a drain tube designed to remove excess fluid from a body cavity, surgical site, or wound. The tube has a central internal passageway and extending portions arranged in opposing pairs, which are configured and spaced to form open channels or grooves between their sidewalls. The external open U-shaped channels thus formed run longitudinally along the outside of the tube. The sloped tubing wall along one sidewall or both sidewalls of one or more of the open channels includes crossholes. These crossholes extend through the sidewalls to provide communication between the channel and the internal central passageway of the drain tube.

In one embodiment of the present invention, an inverted V-shaped rib runs longitudinally along one side of the inner wall of the tube, reaching nearly to the center of the central passageway, thereby providing structural support to prevent the tube from collapsing if compressed. An embodiment may also include a notch shaped to correspond to the V-shaped rib. Such a notch may be formed along the diametrically opposite inner wall of the tube from the V-shaped rib. The notch receives the rib to help resist the collapsing of the tube by twisting.

In contrast to previously known designs for perforated drain tubes, crossholes are positioned along the side walls of the external channel, thereby retarding or preventing tissue from growing into the holes during the time the drain remains in place. The ingrowth of tissue into the holes may also be prevented or retarded by spacing the holes from the top of the channel side walls. Additional crossholes can be positioned within the base of the channel to prevent fluid build up within the channel. If desired, the end of the tube that is not inserted into the wound or body cavity may be connected to a suction device.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 2 is a top view looking directly down on the drain tube of FIG. 1.

FIG. 3 is a cross-sectional view taken along line 3—3 in FIG. 2.

FIG. 4 is a cross-sectional view of an alternate embodiment.

DETAILED DESCRIPTION OF THE PREFERRED EMBODIMENT

Figure 1:
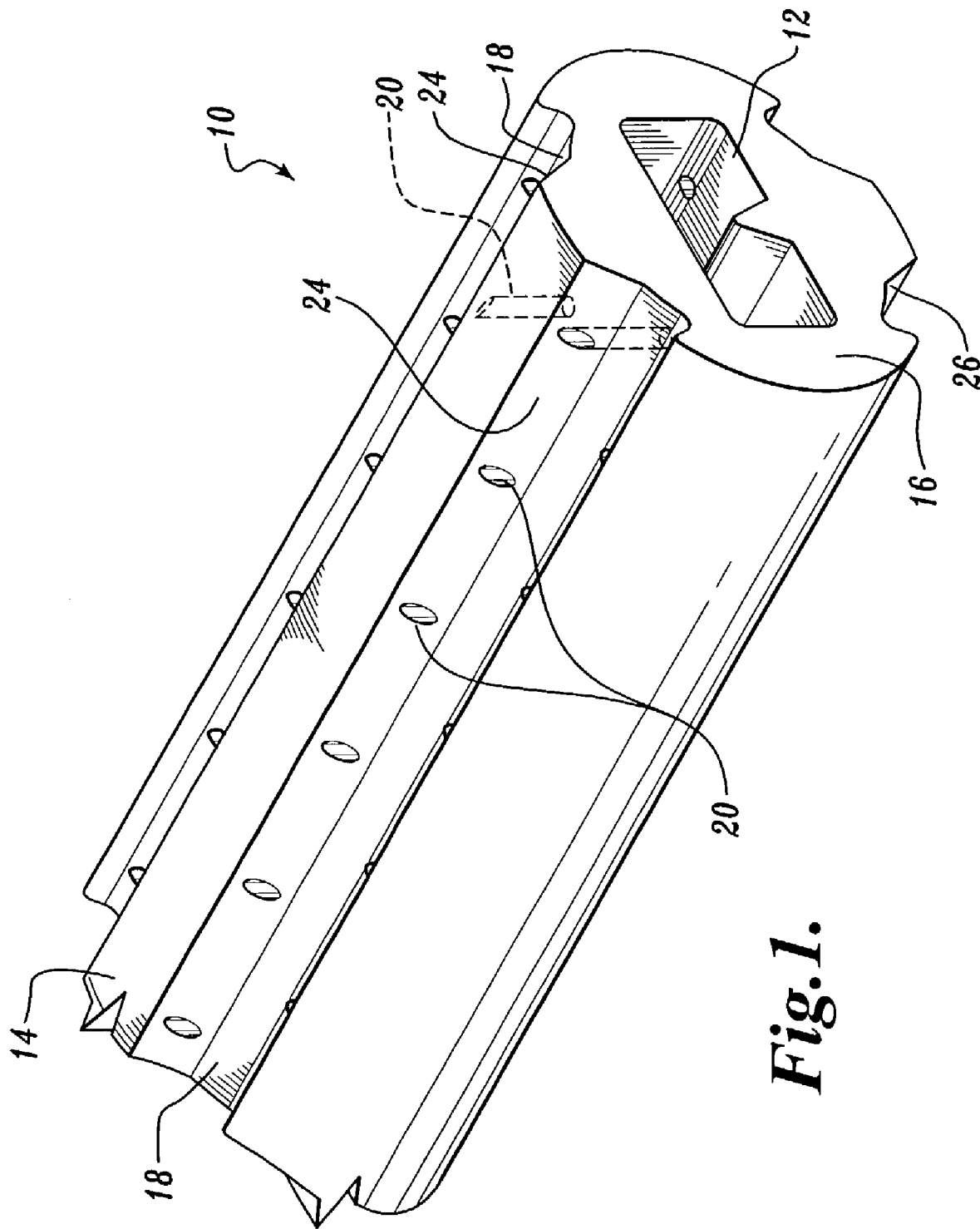
FIG. 1 is a perspective view of a preferred embodiment of the drain tube of the invention.

Referring to the drawings, an embodiment of the present invention is illustrated in FIGS. 1–3. The drain tube 10, shown in the figures, comprises an elongated flexible tube having an internal passageway 12 and a plurality of external open channels or grooves 18. The tube has a proximal end, for inserting into the wound or body cavity, and a distal end that remains outside the wound or body. The external grooves 18 run longitudinally outside of the tube 10 along the length of the tube. In a preferred embodiment, the width across the grooves 18 may be about 1–3 times the depth of the grooves 18. As one specific example, the groove width is about 2.5 times the groove depth. Also, in one specific example, the thickness of the tube wall at the bottom of the open grooves is about 0.2–0.3 mm.

The cross-section of the internal passageway 12 of the drain tube 10 may be rectangular, square, round, ovoid, elliptical, or of other shape. In one of the preferred embodiments, as illustrated in FIGS. 1 and 3, the internal passageway 12 may be generally rectangular. Optimally, the longer side of the rectangular cross-section of this embodiment has a length of about 6–9 mm, while the shorter side has a length of about 4–6 mm. It is preferable but not essential for the inner passageway to be rectangular to aid in forming the drain tube 10 using injection-molding technology. The rectangular cross section allows a rectangular core to be used to present flat surfaces perpendicular to the inward ends of pins placed in the die to form crossholes 20 and 21. When the die is closed, the inward ends of the pins seat securely against the outer surface rectilinear core. Consequently, crossholes 20 and 21 are formed between the outside surface of the drain tube 10 and the inner passageway 12

In an alternate embodiment depicted in FIG. 4, the internal passageway 12' may be generally ovoid in shape, and the ratio of the oval's long and short axes is about 1.3. Optimally, the longer axis of the oval cross-section of this embodiment has a length of about 8–9 mm, while the shorter axis has a length of about 6–7 mm. As one nonlimiting example, a drain tube with an ovoid internal passageway could be formed using extrusion technology. The crossholes 20 and 21 could be formed later by drilling, punching, or similar techniques.

A plurality of portions of the external wall of the tube extend outwardly, and are arranged in opposing pairs 14A, 14B, 16A, and 16B to form between their sidewalls the open channels or grooves 18 that run longitudinally along the outside of the tube. The outwardly extending portions may be similar or dissimilar in size and shape with regards to the percentage of the circumference of the outer wall of the tube from which they extend. In one exemplar embodiment, the protruding portions of the tube wall are dissimilar in size. For example, in one embodiment, each member of a pair of outwardly extending portions 14A, 14B may extend from about 7–8% of the outer circumference of the tube, while each member of the opposing pair 16A, 16B extends from about 20–30% of the outer circumference of the tube, as shown in the figures.

To effect drainage, one end of the tube generally is positioned at the site of a wound or a surgical incision, and the other end is positioned external to the body wall. If desired, the external end of the tube may be attached to a suction device to facilitate the removal of fluids. The open channels 18 perform the function of acting as collecting depots for the fluid that is being drained away from the wound or surgical site.

The sidewalls of the open grooves 18 contain a plurality of crossholes 20 and 21 (FIGS. 1 and 2) whereby the grooves 18 are brought into fluid communication with the internal passageway 12, thereby providing a means for fluid that has collected in the grooves 18 to enter the internal passageway 12 so that it can be carried away from the wound or site of surgery.

In one embodiment of the invention, an internally projecting rib 22 (FIGS. 1 and 3) may run longitudinally along one side of the wall of the inner passageway 12 to project toward the opposite side of the inner passageway 12. The rib 22 provides structural support so that the drain tube 10 will not collapse if it becomes compressed, e.g., due to tissues growing against it, pressure resulting from the body position of the patient, or pressure from swollen tissue pressing against the drain tube 10. In a preferred embodiment, the rib 22 has a cross-sectional shape of an inverted V, but may have any suitable cross-sectional shape.

In an alternate embodiment depicted in FIG. 4, a correspondingly shaped notch 23' is formed along the inner wall of the tube diametrically opposite to the tip of rib 22' to receive the tip of the rib therein thereby to help prevent the tube from collapsing by twisting along its length. The notch 23' is illustrated in FIG. 4 as being of a V-shape to match the shape of the tip of rib 22'.

The longitudinal internal rib 22 enables the tube to resist collapse if suction is applied to the external end of the tube. The distal end of the tube may be connected to a suction device by any convenient means, for example, the tube may be flared at the distal end to facilitate its ability to slide over suction device connectors of various diameters. Alternatively, the tube may be fitted with a plastic or metal nut having a rubber or silicone O-ring to provide a leakproof seal.

The crossholes 20 and 21 connect with the inner passageway 12. Crossholes 20 extend through the sloped wall portions 24 and 26 of the outwardly extending portions 14A and 14B. The crossholes are positioned along the sidewalls 24 and 26 of channels 18 in order to help thwart the ingrowth of tissue into the crossholes, which may be more likely to occur if the crossholes intersected the peripheral portions of the outwardly extending portions 14A or 14B, or outwardly extending portions 16A or 16B. Preferably, the crossholes 20 are spaced from the intersection of the sidewalls 24 and 26 and the outwardmost surfaces 36A and 36B of the extending portions 14A and 14B. In this manner, sections of the sidewalls 38 and 40 exist between the crossholes 20 and the intersection of the sidewalls 24 and 26 and the outwardmost surfaces 36A and 36B as shown in FIGS. 3 and 4.

Preferably, the crossholes 20 are positioned on opposite sides of the sidewalls of at least one outwardly extending portion. Most preferably, a plurality of crossholes are formed on all of the sidewalls 24 and 26 of the smaller outwardly extending portions 14A, 14B. Also, as shown in FIG. 3, ideally, but not essentially, the crossholes 20 extending through the sloped sidewalls 24 of extending portions 14A are in parallel with each other and also parallel with the crossholes 20 extending through the sloped sidewalls 26 of extending portions 14B, thereby to facilitate the formation of the crossholes by molding equipment. It may be possible to align the crossholes toward the central axis of the inner passageway, for example, if the passageways can be incorporated into the tooling die itself.

Crossholes 21 may be included in grooves 18 to allow additional drainage unto the internal passageway 12. Crossholes 21 may be located in the floors 30 and 32 or in the sidewalls of the extending portions 16A and 16B.

The number of crossholes and their positions may vary. In a preferred embodiment, they are evenly spaced and are spaced apart about from 1.5 to 12 mm, and more preferably are spaced apart about 4 to 8 mm. To facilitate manufacture of the drain tube 10, the positions of the crossholes may be staggered as shown in FIGS. 1 and 2. It may also be desirable to stagger the positioning of crossholes 20 and 21 as shown in FIG. 2.

Numerous modifications and variations on the present invention are possible in light of the above teachings. It is therefore to be understood that within the scope of the appended claims, the invention may be practiced otherwise than is specifically described.

The invention claimed is:

1. A drain tube for removing fluids from a wound or from within the body comprising:
   an elongate flexible tube having an internal passageway, a plurality of portions of the external wall of said tube extending outwardly and being arranged in opposing pairs, the walls of the outwardly extending portions forming sidewalls of open external channels that run longitudinally along the length of the tube, the channels having a floor portion between corresponding sidewalls; and
   at least one crosshole extending through the sidewalls of the external channels, but not through the floor portion of the channels, said crossholes providing for fluid communication between said external channel and the internal passageway.

2. The drain tube of claim 1, wherein the number of outwardly extending portions is four.

3. The drain tube of claim 1, wherein the members of at least two of the outwardly extending portions extend from different percentages of the circumference of the tube.

4. The drain tube of claim 3, wherein each member of one opposing pair of outwardly extending portions extends from about 7–8% of the outer circumference of the tube, and each member of the other pair of outwardly extending portions extends from about 20–30% of the circumference of the tube.

5. The drain tube of claim 1, further comprising a rib running longitudinally along one side of the inner wall of the tube and projecting diametrically toward the opposite side of the tube.

6. The drain tube of claim 5, further comprising a notch running longitudinally along the inner wall of the tube substantially diametrically opposite to the rib for receiving the rib within the notch upon sufficient collapse of the tube.

7. The drain tube of claim 1, further comprising a plurality of spaced apart crossholes.

8. The drain tube of claim 7, wherein the crossholes are spaced apart from 1.5–12 mm.

9. The drain tube of claim 8, wherein the crossholes are spaced apart from 4–8 mm.

10. The drain tube of claim 7, wherein the crossholes are positioned on opposite sides of the sidewalls of at least one outwardly extending portion of the tube.

11. The drain tube of claim 10, wherein the crossholes that intercept one sidewall of an outwardly extending portion are staggered relative to the crossholes that intercept the opposite sidewall of the same outwardly extending portion.

12. The drain tube of claim 7, wherein the crossholes extend substantially parallel to each other.

13. The drain tube of claim 1, wherein the internal passageway is ovoid in cross-section.

14. The drain tube of claim 1, wherein the internal passageway is elliptical in cross-section.

15. A drain tube for removing fluids from a wound or from within the body comprising:
   an elongate flexible tube having an internal passageway, at least two portions of the external wall of said tube extending outwardly, the walls of the outwardly extending portions forming the sidewalls of an open external channel that runs longitudinally along the length of the tube;

at least one crosshole positioned on only one sidewall of the external channel and not the other sidewall of the external channel, said crossholes providing for fluid communication between said external channel and the internal passageway;

a proximal end for inserting into the wound or body and a distal end that remains outside the wound or body; and a means for connecting the proximal end of the tube to a suction device.

16. The drain tube of claim 15, further comprising a rib running longitudinally along one side of the inner wall of the tube and projecting diametrically toward the opposite side of the tube.

17. The drain tube of claim 16, further comprising a notch running longitudinal along the inner wall of the tube substantially diametrically opposite to the rib, the notch of a shape corresponding to the shape of the rib.

18. The drain tube of claim 15, wherein the number of outwardly extending portions is four.

19. The drain tube of claim 18, wherein each member of one opposing pair of outwardly extending portions extends from about 7–8% of the outer circumference of the tube, and each member of the other pair of outwardly extending portions extends from about 20–30% of the circumference of the tube.

20. The drain tube of claim 15, further comprising a plurality of spaced-apart crossholes.

21. The drain tube of claim 20, wherein the crossholes are spaced apart from 1.5–12 mm.

22. The drain tube of claim 20, wherein the crossholes are positioned on opposite sides of the sidewalls of at least one external channel, and the crossholes that intercept one sidewall of the external channel are staggered relative to the crossholes that intercept the opposite sidewall of the external channel.

23. The drain tube of claim 20, wherein the crossholes extend substantially parallel to each other.

24. The drain tube of claim 15, wherein the internal passageway is generally ovoid in cross-section.

25. The drain tube of claim 15, wherein the internal passageway is generally elliptical in cross-section.

* * * * *

UNITED STATES PATENT AND TRADEMARK OFFICE
CERTIFICATE OF CORRECTION

| | |
|---|---|
| PATENT NO. | : 7,125,402 B1 |
| APPLICATION NO. | : 10/447722 |
| DATED | : October 24, 2006 |
| INVENTOR(S) | : R. J. Yarger |

It is certified that error appears in the above-identified patent and that said Letters Patent is hereby corrected as shown below:

| COLUMN | LINE | ERROR |
|---|---|---|
| 7 | 16 | "longitudinal along" should read --longitudinally along-- |

Signed and Sealed this

Sixth Day of October, 2009

David J. Kappos
*Director of the United States Patent and Trademark Office*